(12) United States Patent
Charpentier et al.

(10) Patent No.: US 9,523,685 B2
(45) Date of Patent: Dec. 20, 2016

(54) MULTIPLEX METHOD FOR DETECTING AN INFECTION

(71) Applicant: BIO-RAD INNOVATIONS, Marnes la Coquette (FR)

(72) Inventors: Christine Charpentier, Boulogne-Billancourt (FR); Stephane Gadelle, Vauhallan (FR); Nadine Lambert, Chatou (FR); Amparo Sanjuan, Issy-les-Moulineaux (FR)

(73) Assignee: BIO-RAD INNOVATIONS, Marnes la Coquette (FR)

( * ) Notice: Subject to any disclaimer, the term of this patent is extended or adjusted under 35 U.S.C. 154(b) by 240 days.

(21) Appl. No.: 13/892,521

(22) Filed: May 13, 2013

(65) Prior Publication Data

US 2013/0273525 A1  Oct. 17, 2013

Related U.S. Application Data

(63) Continuation of application No. 12/600,297, filed as application No. PCT/EP2008/057111 on Jun. 6, 2008, now abandoned.

(Continued)

(30) Foreign Application Priority Data

Jun. 8, 2007  (FR) ..................... 07 55626

(51) Int. Cl.
   *G01N 33/553* (2006.01)
   *G01N 33/569* (2006.01)
   (Continued)

(52) U.S. Cl.
   CPC .. *G01N 33/56983* (2013.01); *G01N 33/54333* (2013.01); *G01N 33/56911* (2013.01);
   (Continued)

(58) Field of Classification Search
   None
   See application file for complete search history.

(56) References Cited

U.S. PATENT DOCUMENTS

| 4,829,012 A | 5/1989 | Cambiaso et al. |
| 2003/0027205 A1 | 2/2003 | Martinez et al. |

(Continued)

FOREIGN PATENT DOCUMENTS

| CA | 1172561 | 8/1984 |
| EP | 0 194 156 | 9/1986 |

(Continued)

OTHER PUBLICATIONS

Schønau, et al. A one-step solid phase immunoassay for simultaneous detection of serum IgG and IgM antibodies to Borrelia burgdorferi. Journal of Immunological Methods. 1998; 218: 9-17.*

(Continued)

*Primary Examiner* — Janet L Andres
*Assistant Examiner* — Stuart W Snyder
(74) *Attorney, Agent, or Firm* — Saliwanchik, Lloyd & Eisenschenk

(57) ABSTRACT

The invention relates to a method for the in vitro diagnostic detection of an infection with a microorganism, comprising placing a biological sample, in a single assay receptacle, in the presence of particles, each carrying at least one specific detectable physical parameter, and belonging to at least two different groups, one of the groups carrying an anti-IgM capture antibody and the other group carrying a capture antigen derived from said microorganism.

16 Claims, 6 Drawing Sheets

Related U.S. Application Data

(60) Provisional application No. 60/929,061, filed on Jun. 11, 2007.

(51) Int. Cl.
  *G01N 33/543* (2006.01)
  *G01N 33/576* (2006.01)

(52) U.S. Cl.
  CPC ....... *G01N 33/576* (2013.01); *G01N 2333/02* (2013.01); *G01N 2333/10* (2013.01)

(56) References Cited

U.S. PATENT DOCUMENTS

| | | | |
|---|---|---|---|
| 2004/0126904 A1* | 7/2004 | Watkins | G01N 33/537 436/526 |
| 2005/0147961 A1 | 7/2005 | Esser et al. | |

FOREIGN PATENT DOCUMENTS

| | | |
|---|---|---|
| EP | 0304 238 | 2/1989 |
| FR | 2 498 760 | 7/1982 |
| WO | WO 99/63349 | 12/1999 |
| WO | WO 03/095968 | 11/2003 |

OTHER PUBLICATIONS

Dasso et al. A comparison of ELISA and flow microsphere-based assays for quantification of immunoglobulins. J. Immunol. Meth. 2002; 263: 23-33.*

Kuller, et al. Development of a whole-virus multiplex flow cytometric assay for antibody screening of a specific pathogen-free primate colony. Diagnostic microbiology and infectious disease. 2005; 53(3): 185-93.*

Monceyron and Grinde, Detection of Hepatitis-A Virus in Clinical and Environmental Samples by Immunomagnetic Separation and PCR. Journal of Virological Methods. 1994; 46(2): 157-166.*

Written Opinion in International Application No. PCT/EP2008/057111, Sep. 11, 2008, pp. 1-7.

Monceyron, C. et al. "Detection of hepatitis A virus in clinical and environmental samples by immunomagnetic separation and PCR" *Journal of Virological Methods*, 1994, pp. 157-166, vol. 46.

Kuller, L. etal. "Development of a whole-virus multiplex flow cytometric assay for antibody screening of a specific pathogen-free primate colony" *Diagnostic Microbiology and Infectious Disease*, 2005, pp. 185-193, vol. 53.

Schonau, A. et al. "A one-step solid phase immunoassay for simultaneous detection of serum IgG and IgM antibodies to *Borrelia burgdorferi*" *Journal of Immunological Methods*, 1998, pp. 9-17, vol. 218.

Louis, S. et al. "A new and simple non-magnetic technique to highly and rapidly enrich hematopoietic progenitors from mouse bone marrow" *Blood*, Nov. 16, 2001, p. 118b, vol. 98.

Crandall, R. B. et al. "The Relative Proportions of IgG-, IgA- and IgM-containing Cells in Rabbit Tissues during Experimental Trichinosis" *Immunology*, 1967, pp. 147-158, vol. 12.

Garlatti, V. et al. "Cutting Edge: C1q Binds Deoxyribose and Heparan Sulfate through Neighboring Sites of Its Recognition Domain" *Jounral of Immunology*,2010, pp. 808-813, vol. 185.

* cited by examiner

MULTIPLEX METHOD FOR DETECTING AN INFECTION

CROSS-REFERENCE TO RELATED APPLICATIONS

This application is a continuation of U.S. application Ser. No. 12/600,297, filed Nov. 16, 2009, which is the U.S. national stage application of International Patent Application No. PCT/EP2008/057111, filed Jun. 6, 2008, which claims the benefit of U.S. Provisional Patent Application No. 60/929,061, filed Jun. 11, 2007.

The invention relates to the in vitro detection of an infection with an infectious, in particular viral, microorganism. The invention relates to a method for simultaneously detecting total immunoglobulins and immunoglobulins M directed against this same infectious microorganism. The invention relates more particularly to the simultaneous detection of total immunoglobulins and immunoglobulins M directed against a human hepatitis virus.

Infections caused by microorganisms, in particular by viruses such as, for example, the hepatitis virus in humans, constitute in general a preoccupying health problem that has been recognized for a long time, in particular in blood transfusion and in diagnosis.

In general, in order to prevent the uncontrolled propagation of an infectious agent, in particular of a hepatitis virus, it is essential to determine as early as possible whether a sample from a patient or a blood bag for transfusion is contaminated with such an agent or virus. Moreover, it is just as important to be able to follow the patient's immune state throughout the infection in order to determine whether or not the patient has entered into convalescence, and thus to apply the appropriate therapeutic steps and/or an immunization when the latter exists.

The methods for the in vitro detection of this type of infection are most commonly based on the detection by immunoassay (or quantitative immunological determination) of the antibodies directed against the infectious agents. Immunoglobulins M ("IgMs"), which appear early and transiently, are the hallmark of a recent acute, or primary infection. Total immunoglobulins, which group together the various immunoglobulin isotypes (IgM, IgG and IgA) are the hallmark of the chronicity or duration of the infection over time, or else the convalescence phase of the patient. A considerable time after an acute infection, the total immunoglobulins consist predominantly of IgG for supporting long-term immunity (Hollinger et al., Fields Virology, p. 735-785, 1996). For this reason, it is important to be able to differentiate, throughout an infection, between the IgMs and the total immunoglobulins in a patient. This is a very general situation in in vitro serology.

This type of problem is in particular found in the case of infections caused by the hepatitis viruses in humans: infection with the hepatitis A virus, called HAV; infection with the hepatitis B virus, called HBV, etc. A comparable situation is found with other blood viruses in humans: HSV (Herpes simplex virus), CMV (Cytomegalovirus), dengue virus, other flaviviruses (such as the West Nile Virus), the rubella virus, the influenza virus, VZV (Varicella Zoster Virus), etc. with various bacteria (*Treponema pallidum, Borrelia burgdorferi*, etc.), and with various single-cell parasites (*Toxoplasma gondii*, for example).

The detection of total immunoglobulins by the indirect format (reaction of the sample on a solid phase carrying the target antigen, then visualization with a labelled anti-human immunoglobulin antibody) has been known for many years, inter alia, with the pioneering ELISA patents in the 1970s. However, this format is not preferred since it is subject to nonspecific interference, inter alia, with rheumatoid factor, potentially present in the sample tested.

Furthermore, F X Heinz, et al., "Comparison of two different enzyme immunoassays for detection of tick-borne encephalitis virus in serum and cerebrospinal fluid" (*Journal of Clinical Microbiology*, 14: p. 141-146, (1981)), noted the existence, in an indirect EIA assay (immunoenzymatic assay) for detecting IgM, of competition between IgMs and IgGs, which affects the sensitivity and the specificity of the final detection.

The detection of total immunoglobulins by the "double antigen sandwich" format (reaction of the sample carrying immunoglobulins to be detected with a solid phase carrying the antigen, then visualization with a second antigen which is detectably labelled) has been known since 1978 (Maiolini, R. et al.; *Journal of Immunological Methods*, 20 (1978) p. 25-34; and also the French patent application published with FR 2 383 446).

The detection of class-specific immunoglobulins by the "immunoglobulin capture" format has itself also been known for many years. It was described in 1979 by Duermeyer W. et al., (*Journal of Medical Virology* 4 (1979): p. 25-32) for the specific detection of anti-HAV IgMs by ELISA (see also U.S. Pat. No. 4,292,403). The principle of the assay is based on the use of microplate wells coated with anti-human IgM antibodies, to which the blood sample containing the IgMs to be detected is added. After an incubation period, the wells of the microplate are washed and HAV antigen is added in a known amount, and then incubated. Finally, after further washing, any antigen bound to the well is then detected by means of a final incubation carried out in the presence of an antibody (F(ab')$_2$) directed against the HAV antigen and labelled with an enzyme. U.S. Pat. No. 4,273,756 in the same way describes class-specific "immunoglobulin capture" formats for detecting IgAs, IgDs, IgEs, IgGs and IgMs directed against various hepatitis viruses (HAV, HBV).

In general, and beyond diagnosis relating only to HAV, attempts have of course been made, for obvious reasons of cost and simplification, to develop a method for simultaneously detecting the early IgMs and the later IgGs (which generally constitute most of the total immunoglobulins).

As reported by Olli Meurman ("Detection of antiviral IgM antibodies and its problems—A review", in New Developments in Diagnostic Virology, Peter A. Bachmann editor, Springer-Verlag, Berlin Heidelberg New York 1983) and W. Duermeyer (<<A new principle for the detection of specific IgM antibodies applied in an ELISA for hepatitis A>>), (*Journal of Medical Virology* 4 (1979): p. 25-32—above), the attempts made have proven to be time-consuming and too laborious. This is because they involve a preliminary step of separating the various immunoglobulin types, either by zonal or sucrose-gradient ultracentrifugation, or by gel filtration, or by adsorption of IgGs with staphyloccal protein A or with an anti-Fc gamma antibody, or else by cleavage of IgMs with β-mercaptoethanol.

Another alternative is to combine two different visualizations. Angarano et al., (*Journal of Clinical Microbiology*, June 1984, p. 905-910) proposes a system for the simultaneous detection of anti-HBc IgMs and total Igs (essentially IgG), called RIELISA (Radio-Immune Enzyme-Linked-ImmunoSorbent Assay), which combines a competitive radioimmunoassay for detecting the total anti-HBc immunoglobulins (CORAB assay from Abbott Laboratories) with an indirect ELISA immunoassay for detecting the anti-HBc IgMs. In the two assays, the same antigen (recombined HBc antigen) is adsorbed onto a one and only solid phase (polystyrene bead, placed in a well), but, on the one hand, an antibody directed against the HBc antigen and radioactively labelled (iodine$^{125}$) is used for detecting the total anti-HBc immunoglobulins, and, on the other hand, an enzymatically labelled (with peroxydase) anti-IgM antibody is used for detecting the anti-HBc IgMs. Angarano et al. (above) specifies that the only essential point is that the labelling of the antigen-specific antibody should be different and should not interfere with that of the immunoglobulin-class-specific antibody.

It is obvious that the system of Angarano et al., with its two obligatory distinct signal systems (i.e. with two detectable labels) is far from simple: after a first immunological step carried out simultaneously for the two assays, the signals must be measured separately and sequentially and in a complex manner. In fact, the process begins with the measurement of the radioactive first signal, bound to the solid phase, thus reflecting the titres of total anti-HBc immunoglobulins, and then, in a second step, the peroxydase-labelled anti-IgM antibody is added to the bead, followed, after incubation, by the addition of the substrate ($H_2O_2$)+chromogen (OPD) mixture. After incubation and development of the colour, this final reaction is stopped with hydrochloric acid and the final optical density obtained, which reflects the anti-HBc IgM titres, is measured.

In addition, as can be noted, the complex system of Angarano et al., which to its credit clearly differentiates between the total anti-HBc immunoglobulin titres and the anti-HBc IgM titres, nevertheless supposes that specific precautions be taken due to the risks associated with handling radioactive compounds (i.e. iodine$^{125}$). Finally, the methodology of Angarano et al. still has to resort to the prior elimination of the interference by rheumatoid factor (inherent in the indirect immunoassay system used for detecting IgM) by adding heat-aggregated immunoglobulin G in the dilution buffer. All this makes the methodology of Angarano et al. relatively disadvantageous.

Conventionally, the detection of IgMs and IgGs directed against the same virus is mainly carried out by performing two immunoassays on separate side phases, so as to avoid any possible interference between the two assays and to obtain clearly differentiated IgM and IgG signals.

Use has thus been made, in the conventional "immunoglobulin capture" format, of two distinct solid phases, for example two microplate wells according to Duermeyer W. et al. (above) or two nitrocellulose strips according to the technique of Venture Technologies Malaisie (*Médecines et maladies infectieuses* [Medicines and infectious diseases], 33, 2003, p. 396-412). One is coated with anti-IgM antibodies and the other with anti-IgG antibodies, and the sample is added for each of the assays. These techniques therefore require two distinct tests to be carried out, and are therefore relatively disadvantageous.

Moreover, it is possible to use multiple types of techniques for detecting immunoglobulins by immunoassay: in addition to the ELISA and radioimmunoassay mentioned above, there are techniques by immunofluorescence, immunoluminescence, etc., in heterogeneous or homogeneous phase, etc. There are also techniques based on particulate immunoagglutination, the final signal of which can be detected visually or quantified using a detection instrument, inter alia, using an instrument for detection by flow cytometry. One of the well-known advantages of measurement by flow cytometry is that it constitutes a rapid and sensitive means for detecting an analyte.

Flow cytometry is based on the passage of a suspension of microparticles, in the form of a stream, in front of a light ray. Electro-optical sensors make sure that a single particle at a time passes in front of the light ray. The signal caused by the disturbance of the light ray as the particle passes is then detected and recorded.

U.S. Pat. No. 6,872,578 B2 describes in particular a multiplex immunoassay system (i.e. an immunoassay system with simultaneous detection of several analytes in a single sample). This system combines, in a heterogeneous immunoassay, the use of flow cytometry and of several groups of solid particles. These particles are magnetic and each carries a specific detectable parameter (i.e. a physical characteristic such as, for example, a size, a unique colour or else a specific fluorescence). Each group of microparticles comprises a range of values for differentiating the particles into several non-overlapping groups distinguishable by automated detection methods suitable for the parameters in question.

These particles each carry, bound to the surface, a different assay reagent from one group to the other. All the particles of the same group carry the same reagent. The magnetic characteristic of these particles allows the separations of the solid and liquid phases to be automated during the washing.

U.S. Pat. No. 6,872,578 B2 describes, inter alia, an example of simultaneous detection of antibodies of various immunoglobulin classes (IgG and IgM) directed against the rubella virus antigen. In this example, the IgGs and IgMs are immunopurified using a first magnetic particle sensitized with the antigen specific for the IgGs and IgMs to be detected. After this first incubation, the nonspecific immunoglobulins are eliminated during the washing. The specific immunoglobulins, which are captured by the antigen adsorbed onto the particle, are then released into the supernatant by adding acetic acid. This supernatant is then transferred into another tube and the IgGs and IgMs are assayed by means of a sandwich format using solid phases and conjugates consisting of anti-human IgM and anti-human IgG antibodies. This technique is laborious since it requires pretreatment of the sample so as to conserve only the antigen-specific Igs.

It is also possible to use, as is the case with the "Multimetrix *Borrelia* IgG- or IgM-assay" system from the company Multimetrix GmbH, (Heidelberg, Germany), a mixture of particles, each coated with a different recombined *Borrelia* antigen, and differential detection of the IgMs and IgGs by the indirect format using anti-IgG antibodies and anti-IgM antibodies labelled with a fluorescent label (phycoerythrin). The fluorescence of the final complex of each bead is measured by flow cytometry using an analyzer from the company Luminex Corporation. No washing step is required, thereby making it a simplified immunoassay. However, the protocol requires several reaction tubes and several reagents sold under different kit references. This system is presented, according to the commercial brochure obtained, as being sensitive and reliable. The principle for the detection of anti-EBV IgG and IgM antibodies on Bioplex 2200®, described in the publication by Klutts et al. (*Journal of Clinical Microbiology*, November 2004, p. 4996-5000), is identical. As above, it requires two different reagents and the immunoreactions are carried out in two different reaction tubes. These two EBV assays use a mixture of particles, each coated with a different EBV antigen, and differential detection of the IgMs and IgGs by the indirect format using anti-IgG antibodies and anti-IgM antibodies labelled with a fluorescent label (phycoerythrin), using two different kits.

The fluorescence of the final complex of each particle is measured by flow cytometry using a detector from the company Luminex Corporation.

There exists therefore a real need to have a method which is simple to carry out, rapid, sensitive, specific, quantitative or semi-quantitative and reproducible and which can be automated—with a view to screening over the entire duration of the infection and also in pre- and post-immunization follow-up—for detecting and differentiating IgMs and total immunoglobulins (total Igs), completely simultaneously, i.e. using a one and only, non-pretreated sample, in a one and only assay receptacle, in the same number of incubations, using a single signal system, and in a one and only signal reading time.

SUMMARY OF THE INVENTION

The authors of the present invention have therefore endeavored to solve the problem stated above and, for this, to develop an alternative method for simultaneously detecting IgMs and total immunoglobulins directed against one and the same antigen in a one and only receptacle, and using a one and only biological sample, preferably non-pretreated.

The subject of the present invention is thus a method for the in vitro diagnostic detection of an infection with a microorganism, comprising the simultaneous detection of the immunoglobulins G or of the total immunoglobulins and of the immunoglobulins M directed against said microorganism, present in a biological sample, which method comprises the following steps:

a) placing said biological sample, in a single assay receptacle, in the presence of particles, each carrying at least one specific detectable physical parameter, and belonging to at least two different groups, one of the groups carrying an anti-IgM capture antibody and the other group carrying a capture antigen derived from said microorganism, b) incubating the mixture under conditions which allow the formation of immunocomplexes on each group of particles, c) eliminating the immunoglobulins which have not bound to the particles, d) incubating the mixture of step b) with at least one labelled conjugate, said at least one conjugate consisting exclusively of a detection antigen derived from said microorganism, e) eliminating the detection antigen not bound to the immunocomplexes of step b), f) simultaneously detecting, by means of a detector capable of differentiating the two groups of particles mentioned above, the immunocomplexes of step d) on each particle, whereby the presence or absence of immunoglobulins G or total immunoglobulins and/or immunoglobulins M directed against said microorganism is revealed.

According to a specific embodiment, the groups of said particles differ from one another by virtue of fluorochromes, detectable by a suitable detector.

Advantageously, the suitable detector is associated with a flow cytometer.

The labelling of the detection antigen may be direct or indirect. For example, the detection antigen may carry a biotin, which is revealed by the addition of labelled avidin or streptavidin.

Preferably, the microorganism is a human virus, in particular the human hepatitis virus.

A subject of the invention is also a diagnostic kit or a set of reagents for carrying out the detection method, comprising in particular particles, each carrying at least one specific detectable physical parameter, and belonging to at least two different groups, one of the groups carrying an anti-IgM capture antibody and the other group carrying a capture antigen derived from a microorganism to be detected.

DETAILED DESCRIPTION OF THE INVENTION

In order to solve the stated problem, the inventors have first of all carried out a multiplex assay for simultaneous detection, in a single receptacle, of anti-HAV IgG and IgM in a sample (serum or plasma), combining two formats by immunocapture (see the details of the protocol and results in the Experimental section, comparative Example 1, and the assay formats in FIG. 1):

the first with superparamagnetic particles carrying anti-human IgG antibodies, the second with superparamagnetic particles carrying anti-human IgM antibodies.

After incubation (capture of the IgGs and IgMs of the sample and formation of the first immunocomplexes) and a first wash, the HAV antigen was added. After a second incubation, the HAV antigen (Ag HAV) was bound to the two types of complexes formed.

After a second wash, the two reactions were revealed by adding an anti-HAV monoclonal antibody (Mab) coupled to a fluorochrome (phycoerythrin, symbolized PE). After incubation of this conjugate and a third wash, the signal was read by flow cytometry on each particle. The IgM and IgG results were obtained separately through the reading of the signals by the two appropriate laser beams of the flow cytometer.

The IgM detection reached an acceptable sensitivity, even at low concentrations, which represent quite a common situation following an HAV infection.

The sensitivity of the IgG detection was, on the other hand, clearly insufficient, in this configuration, due to the large natural abundance of IgGs (all antigenic specificities included) in the sample. In fact, the anti-IgG superparamagnetic particles were very rapidly saturated with the IgGs not specific for HAV, present in the sample, and no longer captured enough anti-HAV IgG, especially at low concentrations of anti-HAV IgG. This resulted in an insufficient analytical sensitivity.

This is precisely the case in the detection of total anti-HAV immunoglobulins for which there exists a clinical sensitivity threshold essential for the detection of anti-HAV antibodies in the context of post-immunization protection follow-up. This protection threshold has been fixed, by consensus, at 20 mUI/ml, in relation to a WHO-anti-HAV standard (97/646). Below this value, the individual is not protected; above this value, the IgG titre is sufficient to ensure that the individual is protected against the virus.

The inventors therefore designed other assay formats in order to solve the problem of the lack of "IgG sensitivity" described in the above assay.

Entirely surprisingly, the inventors showed that the multiplex combining the two formats described hereinafter for Example 2 (see the details of the protocol and the results in the Experimental section, Example 2, and the assay formats in FIG. 2) is able to simultaneously detect, in a single receptacle, the low IgG concentrations without desensitizing the IgM detection, and, furthermore, makes it possible to differentiate, in a completely sensitive and specific manner, between the anti-HAV IgM antibodies and the total anti-HAV immunoglobulins.

Thus, this method for simultaneously detecting, in a single receptacle, anti-HAV IgG and IgM in a sample (serum or plasma) [which method is therefore the method according to the present invention] combines two assay formats (an "immunoglobulin capture" assay format according to Duermeyer W. et al., for the IgMs and a "double antigen sandwich" assay format according to Maiolini R., et al., for the IgGs):

the first with superparamagnetic particles carrying anti-human IgM antibodies, the second with superparamagnetic particles carrying HAV capture antigen.

After incubation (capture of the IgGs and IgMs of the sample and formation of the first immunocomplexes) and a first wash, a biotinylated HAV antigen is added. After a second incubation, the HAV antigen is bound to the two types of complexes formed.

After a second wash, the two reactions are revealed by adding streptavidin coupled to a fluorochrome (phycoerythrin). After incubation and washing, the signal is read by flow cytometry on each particle. The IgM and IgG results are obtained separately through the reading of the signals by the two appropriate laser beams of the flow cytometer.

The invention, which results in sensitive and differential detection of anti-HAV IgMs and total Igs, is entirely surprising: this is because there was a high risk, with the combination, in a single receptacle, of the two formats according to the method of the invention, that there would be competition for the anti-HAV IgMs of the sample, between the immobilized HAV antigen and the immobilized anti-IgM antibody. In other words, because of the simultaneous implementation of the two formats described above, in one and the same receptacle, there was a risk that some of the anti-HAV IgMs of the sample would be captured (as represented by the dashed arrow in FIG. 2) by the superparamagnetic particles carrying HAV antigen, used precisely for capturing the IgGs, and would no longer be detected as IgM. Such competition would inevitably have resulted in completely insufficient detection of the IgM response (lack of sensitivity) and therefore in it being impossible to detect the IgMs early on. Those skilled in the art would have entirely realized the size of this risk and would therefore have been clearly dissuaded from adopting this combination (multiplex) according to the invention.

The inventors have similarly used the multiplex method according to the invention for simultaneously detecting IgG and IgM antibodies directed against the hepatitis B virus capsid (detection of HB core IgG and IgM antibodies). To this effect, see the Experimental section, Example 3, and the assay formats in FIG. 3.

On this basis, the inventors propose a method for the general detection of IgGs and IgMs, in a multiplex format, that can be adapted to many microorganisms for which it is important, from a diagnostic point of view, to detect IgGs and IgMs.

In the section hereinafter, a certain number of definitions useful for understanding the invention are provided.

DEFINITIONS

In the context of the invention, a "biological sample" preferably consists of a biological fluid, such as blood, plasma, serum, urine, cerebrospinal fluid, saliva, etc. Preferably, the sample is plasma or serum. The test sample is preferably of human origin, but may also originate from an animal for which detection of a microbiological infection is necessary.

The term "multiplex detection" refers, in the context of the present invention, to the simultaneous detection of at least two types of antibodies directed against the same or several infectious microorganism(s), and chosen from the group consisting of immunoglobulins M, G, A, D and E and total immunoglobulins in the blood.

The term "antibody" refers to any whole antibody or functional fragment of an antibody comprising or consisting of at least one antigenic combination site allowing said antibody to bind to at least one antigenic determinant of an antigenic compound.

By way of example of antibody fragments, mention may be made of Fab, Fab' and

F(ab')$_2$ fragments and also scFv chains (Single chain variable fragment), dsFv chains (Double-stranded variable fragment), etc. These functional fragments may in particular be obtained by genetic engineering.

The term "antigenic fragment" or "antigen" is intended to mean all or part of a natural or recombined protein of an infectious microorganism such as the hepatitis A virus, capable of inducing antibody synthesis in an infected patient or in an immunized animal.

In particular, the expression "antigen derived from the microorganism", whether it is for capture or detection, is intended to mean any antigen selected from the group consisting of a lysate of said microorganism, one of its natural antigens that has been semi-purified or purified, a recombined protein, a fragment thereof and a synthetic peptide.

The term "capture antigen" is intended to mean an antigenic fragment attached to a solid phase, which is capable of being recognized by antibodies directed against the microorganism, such as anti-HAV antibodies, and of allowing affinity binding with the latter.

The term "capture antibody" is intended to mean an antibody or a part of an antibody, attached to a solid phase, which is capable of retaining at least one antigenic determinant of an antigenic compound present in a biological sample, by affinity binding.

The anti-IgM capture antibodies and the capture antigens may be attached to the particles by any suitable technique. They may be attached by direct covalence, or noncovalently, in particular by affinity. The direct covalent attachment may be carried out by means of activation of the carboxylic groups present on the particles, involving bonding via hydroxysuccinimide or carbodiimide for example.

The term "detection antigen" is intended to mean a labelled antigen which makes it possible either to detect IgM antibodies by the immunocapture method, or to detect IgG antibodies by the conventional antigen-antibody-antigen sandwich method, also called "double antigen sandwich" method (Maiolini et al. (1978)). The detection antigen may be identical to or different from the capture antigen.

The term "labelled" refers both to direct labelling (by means of fluorochromes, luminescent compounds, etc.) and to indirect labelling (for example, by means of antibodies or antigens, themselves directly labelled, or using reagents of a labelled "affinity pair", such as, but not exclusively, the labelled avidin-biotin pair, etc.).

The production of monoclonal antibodies or polyclonal antibodies which can be used in the context of the invention is the result of conventional techniques.

The monoclonal antibodies may be obtained according to the conventional method of lymphocyte fusion and hybridoma culture described by Köhler and Milstein (*Nature*, 256, p. 495-497 (1975)). Other methods for preparing monoclonal antibodies are also known (Harlow et al. editors, *Antibodies A Laboratory Manual, Cold Spring Harbor Laboratory* (1988)). The monoclonal antibodies may be prepared by immunizing a mammal (for example, a mouse, a rat, a rabbit, or even a human being, etc.) and by using the lymphocyte fusion technique which produces hybridomas (Köhler and Milstein, 1975, above).

Alternative techniques to this customary technique exist. For example, monoclonal antibodies can be produced by expression of a nucleic acid cloned from a hybridoma. Antibodies can also be produced by the phage display technique, by introducing antibody cDNAs into vectors, which are typically filamentous phages (for example, Fuse5 for *E. coli*, Scott et al. (Science, 249, pp. 386-390 (1990)). The latter constitute libraries and exhibit scFv fragments at their surface. Protocols for constructing these antibody libraries are described in Marks et al. (1991) (*J. Mol. Biol.*, 222, pp. 581-597, (1991)).

The polyclonal antibodies can be obtained from the serum of an animal immunized against an antigen of peptide nature, according to the usual protocols.

In general, a polypeptide, in particular a recombined polypeptide, or an oligopeptide, can be used for example as immunogen. According to a conventional protocol, rabbits are immunized with the equivalent of 1 mg of the peptide immunogen according to the procedure described by Benoit et al. [*PNAS USA*, 79, pp. 917-921 (1982)].

The animals are given injections of 200 μg of antigen, at four-week intervals, and are bled 10 to 14 days later. After the third injection, the ability of the antiserum to bind to the iodine-radiolabelled antigenic peptide, prepared by the chloramine-T method, is evaluated. It is then purified by chromatography on an ion exchange column consisting of carboxymethylcellulose (CMC). The antibody molecules collected by elution are then adjusted to the desired concentration by methods well known to those skilled in the art, for example using DEAE Sephadex in order to obtain the IgG fraction.

The term "particles" is intended to mean any particles, preferably approximately spherical in shape (they are then generally called beads), having sizes that may be between 0.3 μm and 100 μm in diameter, and preferably between 0.5 μm and 40 μm. Such particles are manufactured, for example, by the companies Luminex, Merck or Dynal.

The particles preferably consist of polymers which are inert with respect to the constituents of the biological samples; they are solid and insoluble in the samples. The polymers used may be polyesters, polyethers, polyolefins, polyamides, polysaccharides, polyurethanes or celluloses. Binders may also be used in order to give integrity and structure to the particles.

Functional groups may be incorporated with these polymers in order to allow the attachment or coupling of macromolecules of biological interest (proteins, lipids, carbohydrates, nucleic acids). These functional groups, known to those skilled in the art, may be amine functions ($-NH_2$) or ammonium functions ($-NH^{3+}$ or $-NR^{3+}$), alcoholic functions ($-OH$), carboxylic functions ($-COOH$) or isocyanate functions ($-NCO$). The monomers most commonly used for introducing COOH functions into polyolefins are acrylic acid or methacrylic acid.

The attachment of reagents to the surface of the particles can be carried out by electrostatic attractions, affinity interactions, hydrophobic interactions or covalent coupling. Covalent coupling is preferred.

The particles used here can be distinguished in that they carry specific detectable physical parameters, i.e. differential markers for distinguishing them from one another by flow cytometry. Preferably, at least two types of different labels or parameters are used. For example, the particles may be impregnated with one or more dyes (for example fluorescent, luminescent, etc.), where appropriate at various concentrations, or with a label of radioisotope, enzymatic, etc., type (Venkatasubbarao S. "Microarrays-Status and prospects" Trends in Biotechnology December 2004, 22(12): 630-637; Morgan et al, "Cytometric bead array: a multiplexed assay platform with applications in various areas of biology", Clin. Immunol. (2004) 100:252-266). Alternatively, particles of various sizes may be used.

In a preferred embodiment, the distinguishable particles emit luminescent or fluorescent signals. Superparamagnetic fluorescent beads from Luminex may, for example, be used.

These physicochemical properties may also make it possible, during the reaction with the biological sample, to separate the fractions captured by these microparticles from those which are not bound. This separation may be carried out, inter alia, by centrifugation, filtration or magnetization. Separation by magnetization is preferred, and for this, beads containing paramagnetic, ferromagnetic, ferrimagnetic and metamagnetic components may be used. Paramagnetic components are preferred, for instance iron, cobalt, nickel or metal oxides such as $Mn_2O_3$, $Cr_2O$ or $Fe_3O_4$. The amount of magnetic components may be between 2% and 50% (by weight), and preferably between 3% and 25%.

In a preferred embodiment, the present invention uses an immunoassay method which combines flow cytometry with the use of a particulate, preferably superparamagnetic, support as solid phase (using, in one and the same receptacle, several categories or groups of distinct particles).

Each group of particles is specific for an immunoreaction and may be differentiated from the other particles by physicochemical properties (size, particle-size distribution, fluorescence and/or optical density). The property of the superparamagnetic particles facilitates separation between the solid and liquid phases in the washing steps and allows the assays to be automated. However, it is not obligatory for the beads used to be superparamagnetic. As superparamagnetic beads that may be used, mention may in particular be made of those described in U.S. Pat. No. 6,872,578. The final detection phase according to the method of the invention generally comprises:

i) simultaneously reading, by means of a detector capable of differentiating the signals of the two groups of particles mentioned above, the labelled immunocomplexes of step c) on each particle, ii) separately obtaining the results for each group of particles, and iii) interpreting the results as indication of the presence or absence of total immunoglobulins (total Igs) and/or of immunoglobulins M directed against said microorganism.

The particles are preferably subjected to a measurement by flow cytometry, as described, for example, in Luminex patent application WO97/14028. Thus, subgroups of particles carrying a reagent (antibody or antigen) are exposed to a biological sample, each sub-group having one or more classification parameters which make it possible to distinguish the particles of one subgroup with respect to another subgroup. The particles thus exposed to the sample then pass into an examination zone (i.e. a cytometer), where the data relating to the classification parameters (for example, the fluorescence emission intensities), and preferably also the data relating to the presence or absence of a complex formed between the reagent and the analyte of interest, are collected.

Thus, for example, in the case where the particles emit fluorescent signals, after addition of the sample to be assayed and of the specific conjugates (labelled, for example, with a fluorescent label), the fluorescence signal emitted by the immunocomplexes formed on each particle is measured using a particulate flow cytometer with a laser reader (for example, of the Luminex™ apparatus type).

The fluorescence specific for each particle is recorded separately, but simultaneously for all the particles. A totally separate and distinct signal is finally obtained for each group of particles.

The present invention thus makes it possible to obtain, by means of a simple and automatable protocol, two separate and sensitive measurements, one for the IgMs, the other for the total immunoglobulins, directed against the same infectious microorganism.

The present invention is described below, more particularly with a view to the simultaneous detection of IgMs and IgGs (or total Igs) for the hepatitis A virus and for the hepatitis B virus, and for the simultaneous detection of IgMs and IgGs (or total Igs) for *Treponema pallidum*, the infectious bacterial agent responsible for syphilis.

Nevertheless, it goes without saying that the present invention applies broadly to all viruses (HSV, Dengue virus, other flaviviruses, such as the West Nile virus; the rubella and influenza viruses, VZV, CMV, etc.), to all bacteria (*Treponema pallidum, Borrelia burgdorferi*, etc.) and/or to all parasites (*Toxoplasma gondii*, etc.) in which there similarly exists a need to simultaneously detect IgMs and IgGs (or total immunoglobulins), in the same assay receptacle, without any loss of sensitivity.

In the method according to the invention, the sample does not need to undergo a pretreatment such as an enzymatic reaction, digestion or modification, or such as a chemical reaction or modification, or the like, etc. (for example, by zonal or sucrose-gradient ultracentrifugation, gel filtration, IgG adsorption via staphylococcal protein A or via an anti-gamma Fc antibody or else cleavage of the IgMs with β-mercaptoethanol. However, it is possible carry out the method according to the invention on a sample which has undergone such a pretreatment.

The receptacle may be any solid container, for example a test tube, a microplate well or a reaction cuvette made of polypropylene.

The elimination of the unbound reagents may be carried out by any technique known to those skilled in the art, such as washing by means of repeated centrifugation steps or taking advantage of the superparamagnetic nature of the beads, by using magnets.

In a specific embodiment of the method according to the invention, the microorganism is chosen from the group consisting of human viruses, bacteria and parasites, preferably single-cell parasites. In a preferred embodiment of the method according to the invention, the microorganism is chosen from the group consisting of human viruses. In a particularly preferred embodiment of the method according to the invention, the microorganism is chosen from the group consisting of human hepatitis viruses such as the HAV and HBV viruses.

In a preferred embodiment, said microorganism is the human hepatitis A virus (HAV), for which it is then possible to obtain a lower detection limit for total anti-HAV immunoglobulins of approximately 20 mIU/ml.

A subject of the present invention is also a set of reagents for carrying out the method according to the invention.

A subject of the present invention is also a kit of reagents for carrying out the method according to the invention.

The type of simultaneous and combined detection of IgMs directed against an infectious microorganism and of IgG antibodies or total Igs against this same infectious microorganism is, in the context of the present invention, called a "multiplex detection" as opposed to a "simplex detection" (where the IgM and IgG or total Ig detections are carried out independently, i.e. are not combined).

The present invention is also directed towards and encompasses all the variants of a simultaneous detection method, which variants may be obtained by methods that are known per se or can be deduced by those skilled in the art without departing from the spirit of the present invention.

The present invention will now be explained in greater detail with the following examples.

The following figures and examples illustrate the invention without limiting the scope thereof.

FIGURE LEGENDS

EXPERIMENTAL SECTION

Example 1

Method According to the Prior Art

Figure 1:
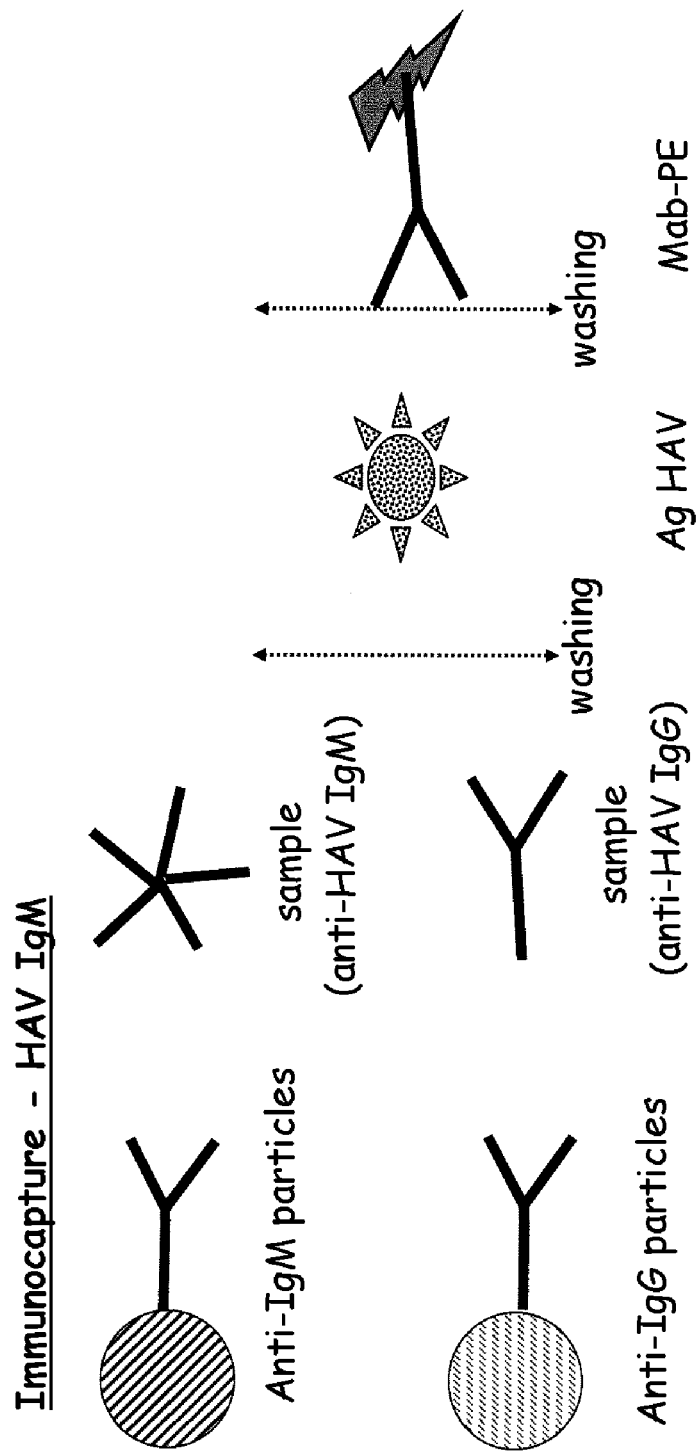
FIG. 1 is a scheme showing the detection of anti-HAV IgGs and IgMs by double immunocapture format (prior art).

The principle of this assay according to the prior art is illustrated in FIG. 1.

Materials and Methods

Materials
1. Analytical System:

The BioPlex 2200® analyzer (Bio-Rad, Marnes la Coquette, France) was used according to the manufacturer's instructions. This automated immunoanalytical device contains a flow cytometer and a Luminex 100™ detector (Luminex Corp., Austin, Tex., United States) and uses heterogeneous sets of superparamagnetic particles. Each group of particles, composed of polystyrene and methacrylic acid (COOH function), and having a size of 8 µm in diameter, is manufactured with various percentages of fluorochromes (CL1 and CL2) producing a unique identification code assigned to each group of particles and detectable by the laser of the Luminex 100™ detector (Luminex Corp., Austin, Tex., United States). After the immunoreaction, the beads pass one by one through a flow cell, at the centre of a liquid matrix, so as to be simultaneously excited and read by two separate lasers. The measurements are carried out as each bead passes through.

The 638 nm red laser excites the identifying fluorochromes (CL1 and CL2) embedded at the surface of each particle and the composite signal is interpreted so as to identify the analyte of the particle. By identifying the category of particle, this laser therefore serves to identify the ongoing assay.

The 532 nm green laser excites the fluorescent probe (conjugate labelled with phycoerythrin (PE)) and the fluorescence emitted is proportional to the conjugate attached to the particle. This laser therefore serves to measure the reactivity of the analyte immobilized on said particle.

The system software converts the signal of the conjugate into a relative fluorescence intensity (RFI) value. The signals are then compared to a standard curve specific to the assay in order to determine the concentration of the analyte. A ratio may also be calculated in order to classify the result qualitatively as positive or negative.

2. Solid Phase:

Two distinct groups of Luminex™ superparamagnetic particles (Luminex Corp., Austin, Tex., United States) were used. Each group of particles is coated with a ligand specific to a particular assay.

Each ligand is coupled using a heterobifunctional reagent.
group 1: anti-human IgM mouse monoclonal antibody (Hytest, Finland) immobilized at 10 μg/mg of particles.
group 2: anti-human IgG mouse monoclonal antibody (Fc gamma; Jackson Immuno Research, United States) immobilized at 20 μg/mg of particles.

3. HAV Antigen:

HAV antigen from Viral Antigen, Memphis, Term., United States.

4. Fluorochrome:

Phycoerythrin from Cyanotech, Hawaii, United States.

5. Conjugate:

Anti-HAV mouse monoclonal antibody (Bio-Rad, Marnes la Coquette, France) coupled to phycoerythrin (PE) using a heterobifunctional reagent, known per se to those skilled in the art.

6. Diluents:

6.1. Superparamagnetic Particle Diluents:

Solution of 20 mM citrate buffer, pH 5.6, containing: 116 mM NaCl, 5.6 mM EDTA, 2% Triton, 10% sheep serum, 0.5 g/l mouse IgG, 0.5% Proclin 300™ (trade mark of the company Supelco), 25% cow's milk (100% skimmed), 0.13% IgG BS3.

6.2. Diluents for the HAV Antigen and for the Conjugate:

Solution of 50 mM phosphate buffer, pH 7.1, containing: 150 mM NaCl; 0.1% $NaN_3$; 1% BSA, 2.75% PEG 6000, 0.1% Tween 20™ (trade mark of the company Sigma), 1% sheep serum, 1 g/l of mouse IgG.

6.3. Diluents for Step 1 or Washing Solution:

Phosphate buffer, pH 7.4, containing: 150 mM NaCl, 0.1% Tween 20™ (trade mark of the company Sigma), 0.034% Proclin 300™ (trade of the company Supelco), 0.095% $NaN_3$.

7. Reaction Cuvettes:

The immunoreactions were carried out in a polypropylene reaction cuvette with a volume of 1 ml.

8. Standards:

The WHO total anti-HAV immunoglobulin standard (code 97/646) was reconstituted according to the recommendations and diluted so as to give the following standard points: 0; 20; 80; 160; 320 and 640 mIU/ml.

Methods

Assay Protocol:

Step 1:

1. The following are successively distributed into each reaction cuvette:
5 μl of sample or of standard+250 μl of diluents for step 1,
10 μl of immunoreactive particles (50:50 mixture of particles of groups 1 and 2)+250 μl of diluents for step 1.

2. After homogenization, the mixture is incubated for 40 minutes at 37° C.

3. The washing steps are then carried out: separation of the solid and liquid phases by magnetization and three successive washes with at least 300 μl of washing solution. At the final wash, the particles are resuspended.

Step 2:

4. 50 μl of HAV antigen (Ag HAV) solution are distributed into each reaction cuvette.

5. After homogenization, the mixture is incubated for 15 minutes at 37° C.

6. The washing steps are then carried out (idem point 3).

Step 3:

7. 50 μl of conjugate (anti-HAV antibody-phycoerythrin, i.e. Mab-PE) are distributed into each reaction cuvette.

8. After homogenization, the mixture is incubated for 15 minutes at 37° C.

9. The washing steps are then carried out (idem point 3).

10. The particles of each well are resuspended by adding to them 35 μl of washing solution with agitation.

11. The particle suspension of each well is drawn off by the flow cytometer.

12. The particle suspension of each cuvette is read using the two laser rays.

13. The results of the readings are directly processed by the flow cytometer and recorded as relative fluorescence intensity units (RFI units).

14. To interpret the results, for each standard point (or sample), a ratio is calculated relative to a cut-off value. In terms of total anti-HAV Igs, the cut-off value corresponds to the RFI value of the standard point at 20 mIU/ml considered to be the protection cut-off.

The ratio of the samples is thus calculated in the following way:

$$\text{Sample ratio} = \frac{\text{mean*of the RFI signal of the sample}}{\text{Cut-off value}}$$

The samples whose ratios are greater than 1 are declared positive, those for which the ratios are less than 1 are declared negative.

All the assays of human samples are carried out in duplicate (as two replicates) and the RFI results used come from the mean of the two replicates.

Results of the Assays Carried Out on the Standard Range

Detection of the IgMs by immunocapture did not pose any problem.

Attention had in particular been paid to the anti-HAV IgG immunocapture format in order to achieve an analytical sensitivity of 20 mIU/ml.

However, in the assays carried out, the immunocapture format for detecting anti-HAV IgGs shows an obvious lack of sensitivity (see Table 1, and graph 1).

This is because the ratios calculated for the standards between 0 and 80 mIU/ml are not significantly different from one another and they are much too close to that of the 20 mIU/ml standard (ratio=1.0) to be reliably selected. The ratios only start to increase, and therefore to be a reflection of total Ig detection, for the standards between 160 and 640 mIU/ml.

TABLE 1

Assaying of the total anti-HAV Ig standard range

| Standard (mIU/ml) | Assaying of IgGs by IgG immunocapture | |
|---|---|---|
| | RFI | Ratio |
| 0 | 19 | 0.79 |
| 10 | 22 | 0.92 |
| 20 | 24 | 1.00 |
| 40 | 29 | 1.21 |
| 80 | 41 | 1.71 |
| 160 | 60 | 2.50 |
| 320 | 89 | 3.71 |
| 640 | 133 | 5.54 |

This lack of sensitivity is due to the fact that the solid phase used (anti-human IgG particles) does not make it possible to specifically capture the IgGs directed against the analyte. The solid phase is therefore saturated by all the other IgGs in the serum.

This phenomenon is not seen in the immunocapture format for the IgMs because it is rare to simultaneously have several infections and to have, in the serum, IgMs directed against various infectious agents during an acute infection.

This immunocapture format was therefore conserved for IgM detection but abandoned for IgG detection and replaced with a sandwich format. The results obtained for the latter format will be described below.

Example 2

Figure 2:
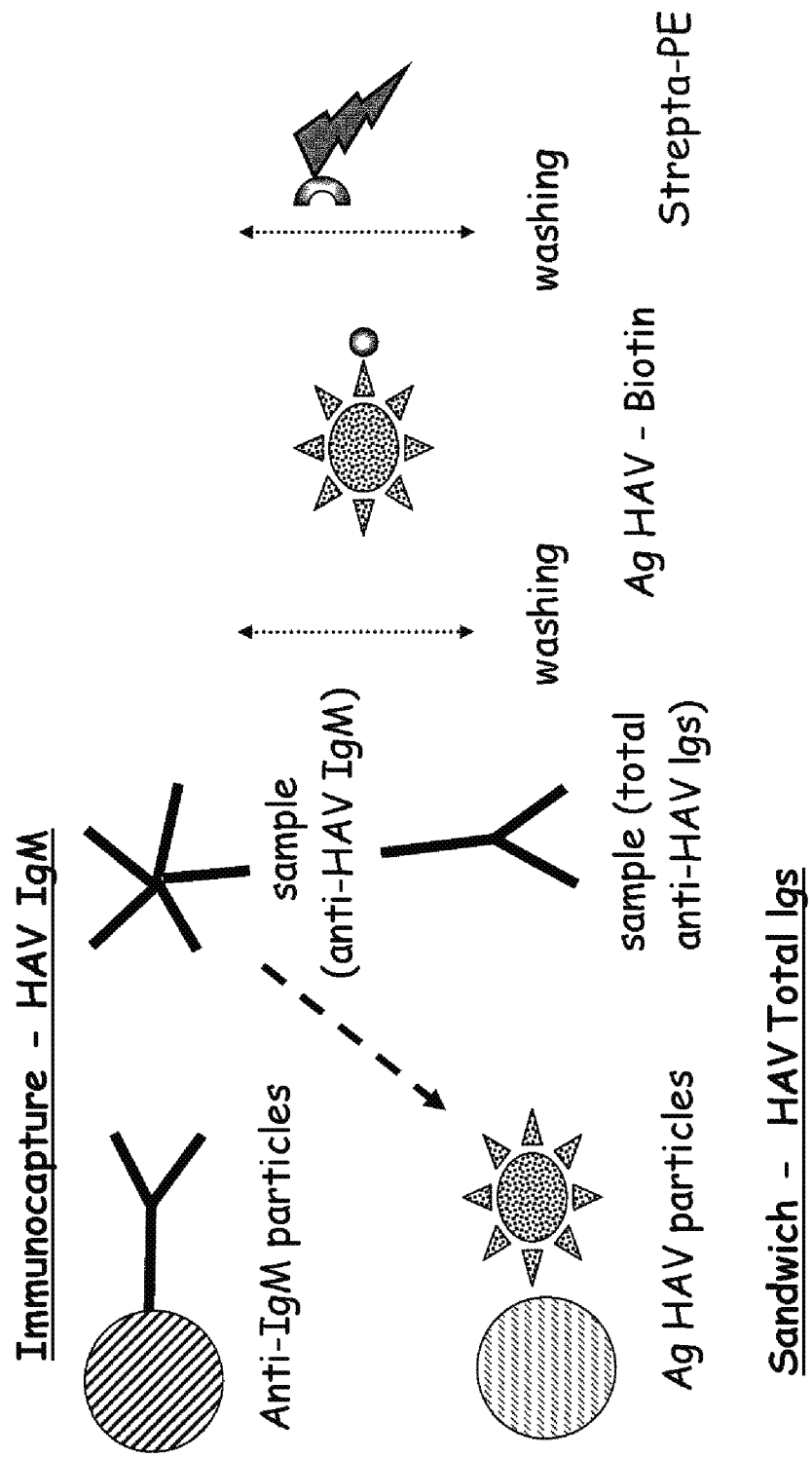
FIG. 2 is a scheme showing the method of the invention for detecting total anti-HAV Igs in sandwich format and anti-HAV IgMs by immunocapture.

Detection Method of the Invention, Applied to the Detection of Anti-HAV Total Igs and IgMs The multiplex detection method according to the invention is described below and in FIG. 2.

Materials and Methods

Materials

The material is essentially identical to that used in example 1, other than the exceptions indicated below.
1. The analytical system: see description of example 1.
2. Solid phase:
Two distinct groups of Luminex™ superparamagnetic particles (Luminex Corp., Austin, Tex., United States) are used:
  group 1: anti-human IgM mouse monoclonal antibody (Hytest, Finland) immobilized at 10 µg/mg of particles;
  group 2: HAV antigen (Viral Ag, Memphis, Tenn., United States) immobilized at 2.5 µg/mg of particles.
3. Conjugate 1:
  HAV antigen (Viral Ag, Memphis, Term., USA) labelled with biotin (Pierce, Rockford, Ill., United States).
4. Conjugate 2:
  Streptavidin (abbreviated to "Strepta", Roche Mannheim, Germany), coupled to phycoerythrin (abbreviated to "PE") from Cyanotech, Hawaii, United States.
5. Diluents:
  The diluents for the beads and for conjugates 1 and 2, the diluent for step 1 and the washing solution are identical to those of example 1.
6. Standards:
  The WHO total anti-HAV immunoglobulin standard (code 97/646) is identical to that used in example 1.
7. Samples:
  The human samples assayed are plasma or serum samples which are positive or negative for anti-HAV total immunoglobulins and/or IgMs. These samples originate from internal sample libraries, made up of specimen bags and from samples sold by the following companies:
    ABO Pharmaceuticals—7930 Arjons Drive, Suite A, San Diego, Calif. 92126, United States,
    Teragenix—5440 NW 33rd Avenue, Suite 108, Ft. Lauderdale, Fla. 33309, United States,
    PromedDx—10 Commerce Way, Norton, Mass. 02766, United States,
    Zeptometrix Corporation—872 Main St., Buffalo, N.Y. 14202, United States,
    BBI Diagnostoc—375 West Street, West Bridgewater, Mass. 02379, United States,
    Life Sera—780 Park North Blvd, Suite 100, Clarkston, Ga. 30021, United States.
  The human samples assayed can be divided up into:
    30 samples negative for anti-HAV total immunoglobulins and IgM (double negatives).
    26 samples positive for total anti-HAV immunoglobulins and negative for anti-HAV IgM.
    15 samples positive for anti-HAV IgM and negative for total anti-HAV immunoglobulins.

Methods

Assay Protocols:
  In the assays described hereinafter, three assay protocols are implemented: the multiplex protocol according to the invention (i.e. the total Ig protocol+the IgM protocol) and two unit protocols (a total Ig protocol and an IgM protocol). These three protocols are identical except for the step of adding the immunoreactive superparamagnetic particles which are used. The multiplex protocol uses the two groups of beads and each unit protocol uses a single group of beads. The amount of particles of group 1 (carrying anti-IgM antibodies) used in the IgM unit protocol and the multiplex protocol remains the same. Similarly, the amount of particles of group 2 (carrying HAV antigen) used in the total Ig unit protocol and the multiplex protocol remains the same.
A. Unit Protocol for Detecting Total Anti-HAV Igs
Step 1:
1. The following are successively distributed into each reaction cuvette:
25 µl of sample or of standard+225 µl of diluents for step 1, 10 µl of immunoreactive particles of group 2 (HAV antigen)+250 µl of diluents for step 1.
2. After homogenization, the mixture is incubated for 40 minutes at 37° C.
3. The washing steps are then carried out: idem point 3 of example 1.
Step 2:
4. 50 µl of solution of conjugate 1 (biotinylated HAV antigen, i.e. "Ag HAV biotin") are distributed into each reaction cuvette.
5. After homogenization, the mixture is incubated for 15 minutes at 37° C.
6. The washing steps are then carried out: idem point 3.
Step 3:
7. 50 µl of conjugate 2 (streptavidin-phycoerythrin, i.e. "Strepta-PE") are distributed into each reaction cuvette.
8. After homogenization, the mixture is incubated for 15 minutes at 37° C.
9. The washing steps are then carried out: idem point 3.
10. The particles of each reaction cuvette are resuspended by adding to them 35 µl of washing solution with agitation.

11. The particle suspension of each reaction cuvette is drawn off by the flow cytometer.
12. The particle suspension of each cuvette is read using the two laser rays.
13. The results of the readings are directly processed by the flow cytometer and recorded in Relative Fluorescence Intensity units (RFI units).
14. To interpret the results, for each standard point or sample, a ratio is calculated relative to a cut-off value. In terms of total anti-HAV Igs, the cut-off value corresponds to the RFI value of the standard point of 20 mIU/ml considered to be the protection cut-off.

The ratio of the samples is thus calculated in the following way:

Sample ratio=mean*of the RFI signal of the sample / Cut-off value

The samples whose ratios are greater than 1 are declared positive, those for which the ratios are less than 1 are declared negative.

All the assays of human samples are carried out in duplicate (as two replicates) and the RFI results used come from the mean of the two replicates.

B. Unit Protocol for Detecting Anti-HAV Ig Ms
Step 1:
1. The following are successively distributed into each reaction cuvette:
25 µl of sample or of standard+225 µl of diluents for step 1, 10 µl of immunoreactive particles of group 1 (anti-IgM antibodies)+250 µl of diluents for step 1.
All the other steps (2-13) of the IgM unit protocol are rigorously identical to steps 2-13 of the total Ig unit protocol.
14. For the calculation of the sample ratios, in terms of HAV IgM, the cut-off value is the mean of the RFIs of the negative samples+12 standard deviations.
The sample ratio calculated is thus the following:

Sample ratio=mean*of the RFI signal of the sample / cut-off value

The samples whose ratios are greater than 1 are declared positive, those for which the ratios are less than 1 are declared negative.

All the assays of human samples are carried out in duplicate (as two replicates) and the RFI results used come from the mean of the two replicates.

C. Multiplex Protocol According to the Invention (Simultaneous Detection of Anti-HAV Total Igs and IgMs):
Step 1:
1. The following are successfully distributed into each reaction cuvette: 25 µl of sample or of standard+225 µl of diluents for step 1,
10 µl of immunoreactive particles (50:50 mixture of particles of groups 1 and 2)+250 µl of diluents for step 1.
All the other steps (2-14) of the multiplex protocol are rigorously identical to steps 2-14 of the total Ig and IgM unit protocols.

Figure 4:
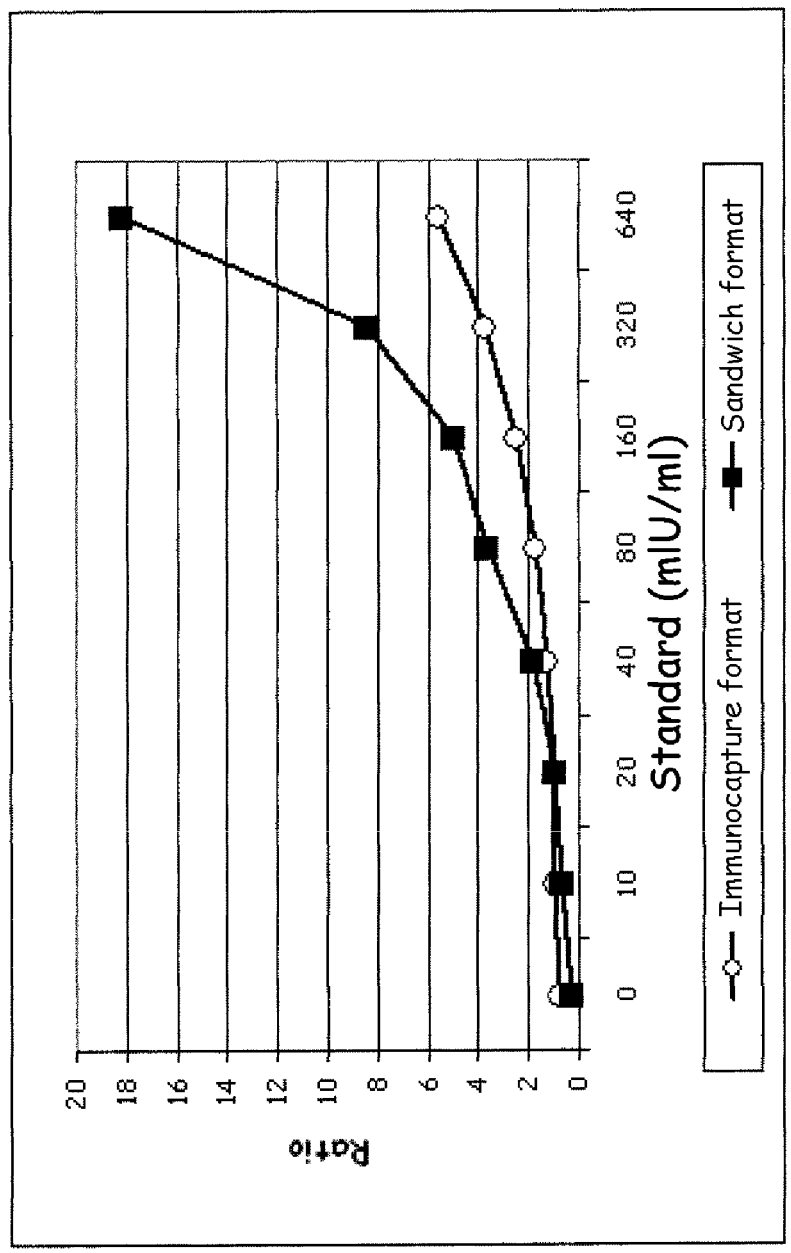
FIG. 4 is a graph showing a comparison of the standard ranges for total anti-HAV Igs assayed by IgG unit format (immunocapture) and by total Ig unit sandwich format.

Results Obtained:
1. Calibration Ranges:
1.1. Total Anti-HAV Ig Standard Range Assayed by Unit Sandwich:

The results obtained with the standard range (0 to 640 mIU/ml) carried out by unit sandwich show that the total Ig sandwich format is much more sensitive than the IgG immunocapture format for example 1 (see table 2, and FIG. 4).

TABLE 2

Comparison of the total anti-HAV Ig standard range assayed by IgG unit immunocapture format (example 1) and by total Ig unit sandwich format (example 2)

| Standard (mIU/ml) | Unit IgG immunocapture format (example 1) | | Unit total Ig sandwich format (example 2) | |
|---|---|---|---|---|
| | RFI | Ratio | RFI | Ratio |
| 0 | 19 | 0.79 | 53 | 0.32 |
| 10 | 22 | 0.92 | 115 | 0.70 |
| 20 | 24 | 1.00 | 165 | 1.00 |
| 40 | 29 | 1.21 | 307 | 1.86 |
| 80 | 41 | 1.71 | 604 | 3.66 |
| 160 | 60 | 2.50 | 820 | 4.97 |
| 320 | 89 | 3.71 | 1403 | 8.50 |
| 640 | 133 | 5.54 | 2994 | 18.15 |

1.2. Total Anti-HAV Ig Standard Range Assayed by Multiplex

Figure 5:
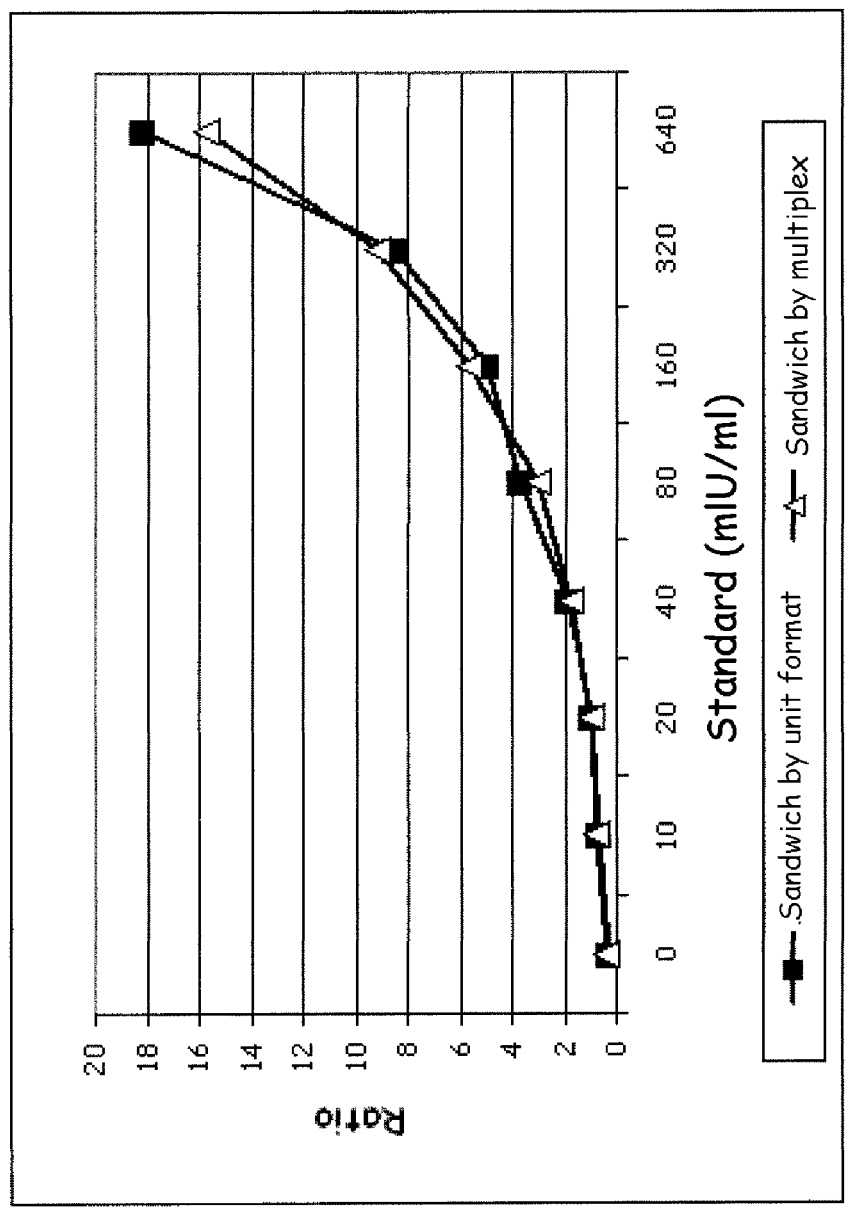
FIG. 5 is a graph showing a comparison of the standard ranges for total anti-HAV Igs assayed by unit sandwich format and by multiplex.

The results obtained with the standard range carried out by sandwich according to the multiplex protocol according to the invention are reported in table 3 and FIG. 5.

TABLE 3

Comparison of the total Ig standard ranges by unit sandwich format and by multiplex

| Standard (mIU/ml) | Unit total Ig sandwich format | | Multiplex total Ig sandwich format | |
|---|---|---|---|---|
| | RFI | Ratio | RFI | Ratio |
| 0 | 53 | 0.32 | 53 | 0.35 |
| 10 | 115 | 0.70 | 112 | 0.75 |
| 20 | 165 | 1.00 | 150 | 1.00 |
| 40 | 307 | 1.86 | 260 | 1.73 |
| 80 | 604 | 3.66 | 449 | 2.99 |
| 160 | 820 | 4.97 | 852 | 5.68 |
| 320 | 1403 | 8.50 | 1372 | 9.15 |
| 640 | 2994 | 18.15 | 2353 | 15.69 |

It is noted that the sensitivity of the multiplex total Ig sandwich format remains unchanged relative to the sensitivity obtained by unit sandwich format.

2. Samples:
2.1. Assaying of the Samples for Total Anti-HAV Igs by Unit Sandwich and by Multiplex Sandwich:

The results obtained with the human samples for total anti-HAV Igs are reported in table 4.

TABLE 4

Comparison of the assaying of samples for total anti-HAV Igs by unit sandwich format and by multiplex according to the invention

| | Unit total Ig sandwich format | | Multiplex total Ig sandwich format | |
|---|---|---|---|---|
| | RFI | Ratio | RFI | Ratio |
| Cut-off value RFI standard at 20 mIU/ml | 165 | 1.00 | 150 | 1.00 |
| Samples negative for HAV IgG and HAV IgM Mean (n = 30) | 39 | 0.24 | 46 | 0.30 |

TABLE 4-continued

Comparison of the assaying of samples for total anti-HAV Igs by unit sandwich format and by multiplex according to the invention

| | | Unit total Ig sandwich format | | Multiplex total Ig sandwich format | |
|---|---|---|---|---|---|
| | | RFI | Ratio | RFI | Ratio |
| Samples positive for HAV IgG and negative for HAV IgM (n = 26) | 1 | 1767 | 10.71 | 2208 | 14.72 |
| | 2 | 2576 | 15.61 | 4106 | 27.37 |
| | 3 | 1793 | 10.87 | 1382 | 9.21 |
| | 4 | 2172 | 13.16 | 3829 | 25.53 |
| | 5 | 1732 | 10.50 | 2763 | 18.42 |
| | 6 | 2229 | 13.51 | 3344 | 22.29 |
| | 7 | 2051 | 12.43 | 3245 | 21.63 |
| | 8 | 2755 | 16.70 | 4612 | 30.75 |
| | 9 | 1755 | 10.63 | 2503 | 16.69 |
| | 10 | 3479 | 21.08 | 4898 | 32.65 |
| | 11 | 2601 | 15.76 | 3429 | 22.86 |
| | 12 | 2338 | 14.17 | 4014 | 26.76 |
| | 13 | 3008 | 18.23 | 4362 | 29.08 |
| | 14 | 3296 | 19.98 | 4034 | 26.89 |
| | 15 | 2447 | 14.83 | 2468 | 16.45 |
| | 16 | 1676 | 10.16 | 1809 | 12.06 |
| | 17 | 714 | 4.32 | 622 | 4.15 |
| | 18 | 2325 | 14.09 | 4392 | 29.28 |
| | 19 | 1385 | 8.39 | 1300 | 8.67 |
| | 20 | 2871 | 17.40 | 3668 | 24.45 |
| | 21 | 2565 | 15.55 | 3011 | 20.07 |
| | 22 | 2315 | 14.03 | 2611 | 17.41 |
| | 23 | 2998 | 18.17 | 3555 | 23.70 |
| | 24 | 1904 | 11.54 | 3259 | 21.73 |
| | 25 | 2250 | 13.64 | 4644 | 30.96 |
| | 26 | 1853 | 11.23 | 3190 | 21.27 |

Very good discrimination is noted between the negative samples (n=30) and the positive samples (n=26) in the total anti-HAV Ig sandwich assay, irrespective of whether it is carried out by unit format or by multiplex according to the invention.

These results therefore show that the detection of total anti-HAV Igs is not desensitized in the multiplex method according to the invention.

All the positive samples are indeed found positive by the method according to the invention, which thus makes it possible to also obtain good clinical sensitivity.

2.2. Assaying of Samples for Anti-HAV IgM by Unit and Multiplex Immunocapture Format:

The results obtained with the human samples for anti-HAV IgM are reported in table 5.

TABLE 5

Comparison of the assaying of samples for anti-HAV IgM by unit immunocapture format and multiplex immunocapture format according to the invention

| | Unit IgM immunocapture format | | Multiplex IgM immunocapture format | |
|---|---|---|---|---|
| | RFI | Ratio | RFI | Ratio |
| Cut-off value mean negatives + 12 SD | 655 | 1.00 | 653 | 1.00 |
| Samples negative for HAV IgG and HAV IgM Mean (n = 30) | 76 | 0.12 | 75 | 0.12 |
| Samples positive for HAV IgG and negative for HAV IgM Mean (n = 26) | 72 | 0.17 | 89 | 0.14 |

TABLE 5-continued

Comparison of the assaying of samples for anti-HAV IgM by unit immunocapture format and multiplex immunocapture format according to the invention

| | | Unit IgM immunocapture format | | Multiplex IgM immunocapture format | |
|---|---|---|---|---|---|
| | | RFI | Ratio | RFI | Ratio |
| Samples positive for HAV IgM and negative for HAV IgG (n = 15) | 1 | 9978 | 15.23 | 8605 | 13.18 |
| | 2 | 12090 | 18.46 | 12389 | 18.97 |
| | 3 | 17619 | 26.90 | 16789 | 25.71 |
| | 4 | 13037 | 19.90 | 14024 | 21.48 |
| | 5 | 8923 | 13.62 | 8658 | 13.26 |
| | 6 | 20325 | 31.03 | 17150 | 26.26 |
| | 7 | 15444 | 23.58 | 13629 | 20.87 |
| | 8 | 15047 | 22.97 | 13561 | 20.77 |
| | 9 | 20611 | 31.47 | 19929 | 30.52 |
| | 10 | 15374 | 23.47 | 14068 | 21.54 |
| | 11 | 16774 | 25.61 | 20497 | 31.39 |
| | 12 | 19430 | 29.66 | 18986 | 29.08 |
| | 13 | 9501 | 14.51 | 13334 | 20.42 |
| | 14 | 16785 | 25.63 | 16113 | 24.68 |
| | 15 | 12647 | 19.31 | 16708 | 25.59 |

Very good discrimination is noted between the samples negative for anti-HAV IgM (n=30+26) and the samples positive for anti-HAV IgM (n=15) in the anti-HAV IgM assay by immunocapture, irrespective of whether it is carried out by unit format or by multiplex according to the invention.

These results thus show that the detection of IgMs by immunocapture is not desensitized by the combination with the sandwich assay in the multiplex method according to the invention.

All the positive samples are indeed found to be positive by the method according to the invention, which thus makes it possible to also obtain good clinical sensitivity.

Example 3

Figure 3:
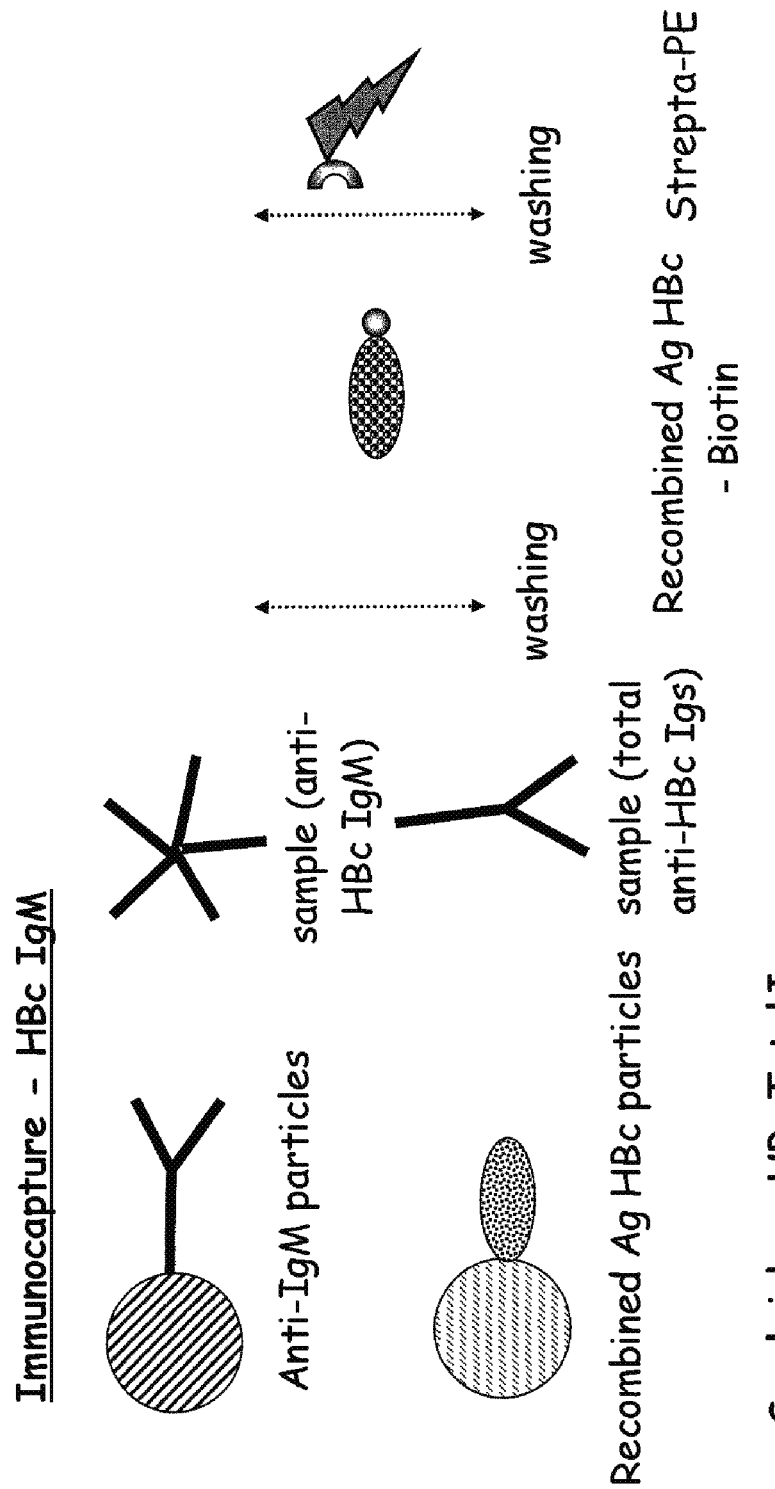
FIG. 3 is a scheme showing the method of the invention for detecting total anti-HBc Igs in sandwich format and anti-HBc IgMs by immunocapture.

Detection Method of the Invention, Applied to the Detection of Anti-HBc Total Igs and IgMs The multiplex detection method according to the invention was also used for assaying anti-HBc total Igs and IgMs. This method is illustrated in FIG. 3 and described below.

Materials and Methods

Materials:

The material used is equivalent to that of example 2, with the exception of the particles, of biotinylated conjugate 1 and of the samples tested.

1. Solid Phase:

Two distinct groups of Luminex™ superparamagnetic particles (Luminex Corp., Austin, Tex., United States) are used.

group 1: anti-human IgM goat polyclonal antibody (Bio-Rad, Marnes la Coquette) immobilized at 10 µg/mg of particles;

group 2: recombined HB antigen (Virogen, Watertown, Mass., United States) immobilized at 10 µg/mg of particles.

2. Conjugate 1:

Recombined HBc antigen (Biokit, Barcelona, Spain) labelled with biotin (Pierce, Rockford, Ill., United States).

3. Samples:

The human samples assayed are plasma or serum samples that are positive or negative for total anti-HBc immunoglobulins and/or anti-HBc IgM. These samples come from internal sample libraries, from samples sold by the companies:

ABO Pharmaceuticals—7930 Arjons Drive, Suite A, San Diego, Calif. 92126, United States, PromedDx—10 Commerce Way, Norton, Mass. 02766, United States, Zeptometrix Corporation—872 Main St., Buffalo, N.Y. 14202, United States.

The human samples assayed can be divided up into:
- 10 samples negative for total anti-HBc immunoglobulins and anti-HBc IgM (double negatives).
- 10 samples positive for total anti-HBc immunoglobulins and negative for anti-HBc IgM.
- 10 samples positive for anti-HBc IgM and negative for total anti-HBc immunoglobulins.

Methods
Assay Protocols:

The protocols used are identical to protocols A, B and C described above in example 2, with the exception of the sample volume used in step 1, which is 5 µl+250 µl of diluent for step 1.

The other steps are identical, including the interpretation step. For the assaying of total anti-HBc Igs and anti-HBc IgMs, the cut-off value is the mean of the RFIs of the negative samples+12 standard deviations.

The sample ratio calculated relative to the cut-off value is thus the following:

Sample ratio=mean*of the RFI signal of the sample cut-off value

The samples whose ratios are greater than 1 are declared positive, those for which the ratios are less than 1 are declared negative.

All the assays of human samples are carried out in duplicate (as two replicates) and the RFI results used come from the mean of the two replicates.

Results Obtained:

TABLE 6

Comparison of the assaying of samples for total anti-HBc Igs by unit sandwich format and by multiplex according to the invention

| | | Unit total Ig sandwich format | | Multiplex total Ig sandwich format | |
|---|---|---|---|---|---|
| | | RFI | Ratio | RFI | Ratio |
| Cut-off value mean negatives + 12 SD | | 202 | 1.00 | 231 | 1.00 |
| Samples negative for total HBc Igs and HBc IgM Mean (n = 10) | | 52 | 0.25 | 54 | 0.26 |
| Samples positive for total HBc Igs and negative for HBc IgM (n = 20) | 1 | 1035 | 5.12 | 1027 | 4.44 |
| | 2 | 2151 | 10.63 | 2225 | 9.61 |
| | 3 | 1161 | 5.74 | 1334 | 5.76 |
| | 4 | 1577 | 7.79 | 1596 | 6.90 |
| | 5 | 2345 | 11.59 | 2134 | 9.22 |
| | 6 | 3499 | 17.29 | 3238 | 13.99 |
| | 7 | 1672 | 8.26 | 1316 | 5.69 |
| | 8 | 492 | 2.43 | 375 | 1.62 |
| | 9 | 3892 | 19.24 | 2435 | 10.52 |
| | 10 | 1565 | 7.74 | 1228 | 5.31 |
| | 11 | 682 | 3.37 | 1042 | 4.50 |
| | 12 | 1198 | 5.92 | 1705 | 7.37 |
| | 13 | 630 | 3.11 | 1408 | 6.08 |
| | 14 | 1188 | 5.87 | 2291 | 9.90 |
| | 15 | 2318 | 11.46 | 3311 | 14.31 |
| | 16 | 2402 | 11.87 | 3550 | 15.34 |
| | 17 | 3887 | 19.21 | 3888 | 16.80 |
| | 18 | 2020 | 9.98 | 2414 | 10.43 |
| | 19 | 1039 | 5.13 | 1720 | 7.43 |
| | 20 | 1334 | 6.59 | 1700 | 7.34 |

Very good discrimination is noted between the negative samples (n=10) and the positive samples (n=20) in the total anti-HBc Ig sandwich assay, irrespective of whether it is carried out by unit format or by multiplex according to the invention.

These results thus show that the detection of total anti-HBc Igs is not desensitized in the multiplex method according to the invention.

All the positive samples are indeed found to be positive by the method according to the invention, which thus makes it possible to also obtain good clinical sensitivity.

TABLE 7

Comparison of the assaying of samples for anti-HBc IgM by unit immunocapture format and by multiplex immunocapture format according to the invention

| | | Unit IgM immunocapture format | | Multiplex IgM immunocapture format | |
|---|---|---|---|---|---|
| | | RFI | Ratio | RFI | Ratio |
| Cut-off value mean negatives + 12 SD | | 321 | 1.00 | 431 | 1.00 |
| Samples negative for total HBc Igs and HBc IgM Mean (n = 10) | | 99 | 0.35 | 112 | 0.32 |
| Samples positive for total HBc Igs and negative for HBc IgM Mean (n = 10) | | 135 | 0.42 | 155 | 0.36 |
| Samples positive for HBc IgM and negative for total HBc Ig (n = 10) | 1 | 3852 | 12.01 | 3239 | 7.52 |
| | 2 | 3687 | 11.50 | 3275 | 7.60 |
| | 3 | 2273 | 7.09 | 1549 | 3.60 |
| | 4 | 1697 | 5.29 | 1501 | 3.49 |
| | 5 | 2333 | 7.27 | 1570 | 3.64 |
| | 6 | 1302 | 4.06 | 1058 | 2.46 |
| | 7 | 5462 | 17.03 | 5813 | 13.50 |
| | 8 | 2595 | 8.09 | 3110 | 7.22 |
| | 9 | 1515 | 4.72 | 1857 | 4.31 |
| | 10 | 1128 | 3.52 | 1132 | 2.63 |

Very good discrimination is noted between the samples negative for anti-HBc IgM (n=10+10) and the samples positive for anti-HBc IgM (n=10) in the anti-HBc IgM immunocapture assay, irrespective of whether it is carried out by unit format or by multiplex according to the invention.

These results thus show that the detection of IgMs by immunocapture is not desensitized by the combination with the sandwich assay in the multiplex method according to the invention.

All the positive samples are indeed found to be positive by the method according to the invention, which thus makes it possible to also obtain good clinical sensitivity.

Example 4

Figure 6:
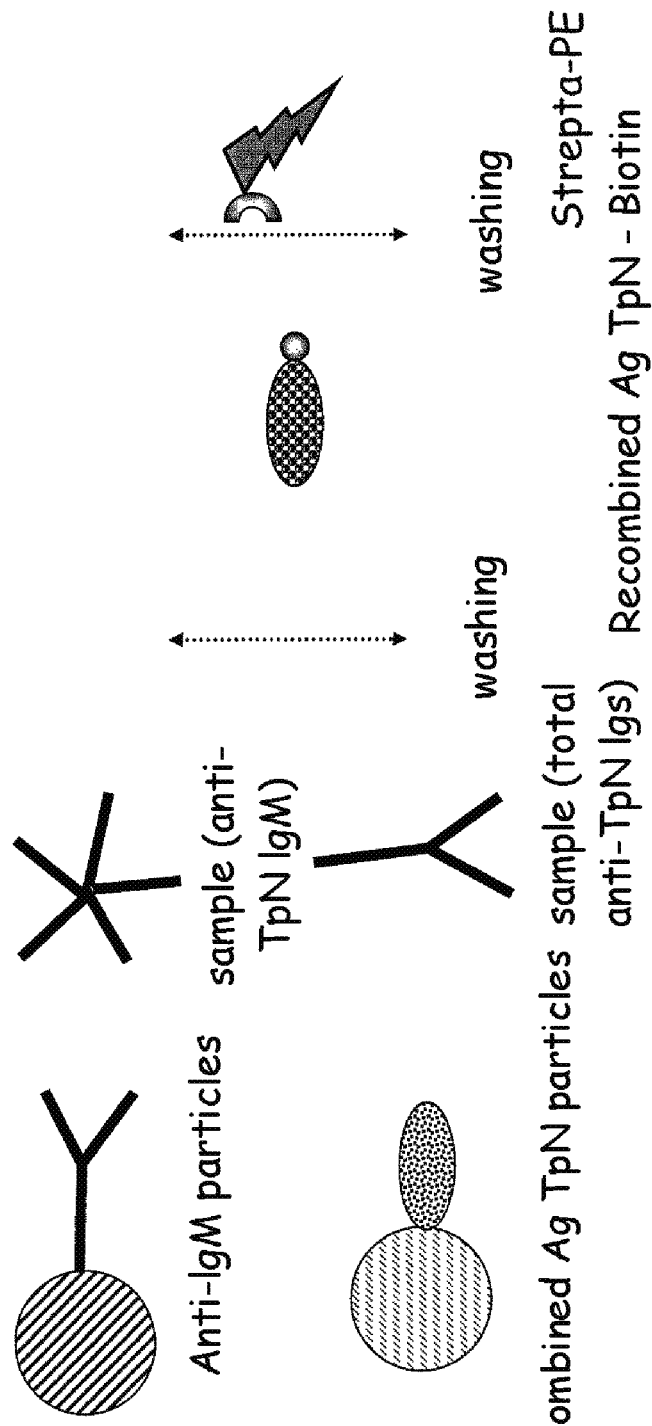
FIG. 6 is a scheme showing the method of the invention for detecting total anti-*Treponema pallidum* Igs in sandwich format and anti-*Treponema pallidum* IgMs by immunocapture.

Detection Method of the Invention, Applied to the Detection of Anti-Syphilis Total Igs and IgMs The multiplex detection method according to the invention was also used for assaying total anti-*Treponema pallidum* Igs and anti-*Treponema pallidum* IgMs, *Treponema pallidum* being an infectious bacterial agent responsible for syphilis. This method is illustrated in FIG. 6 and described below.

Materials and Methods

Materials:
The material used is equivalent to that of examples 2 and 3, with the exception of the particles, of biotinylated conjugate 1 and of the samples tested.
1. Solid Phase:
Two distinct groups of Luminex™ superparamagnetic particles (Luminex Corp., Austin, Tex., United States) are used.
  group 1: anti-human IgM mouse monoclonal antibody (Hytest, Finland) immobilized at 2.5 µg/mg of particles;
  group 2: recombined antigens TpN17 and TpN47 of *Treponema pallidum* (New Market Laboratories Ltd, Kentford, England) immobilized, respectively at 5 µg/mg and 1.25 µg/mg of particles.
2. Conjugate 1:
Recombined antigens TpN17 and TpN47 (New Market Laboratories Ltd, Kentford, England) labelled with biotin (Pierce, Rockford, Ill., United States).
3. Samples:
The human samples assayed are plasma or serum samples that are positive or negative for total anti-*Treponema pallidum* immunoglobulins and/or anti-*Treponema pallidum* IgM.

These samples come from internal sample libraries:
Etablissement Français du Sang (EFS) [French blood bank]—83 rue des Alpes, 94150 Rungis, France,
or from samples sold by the companies:
PromedDx—10 Commerce Way, Norton, Mass. 02766, United States,
SeraCare Life Science—375 West Street, West Bridgewater, Mass. 02379, United States.
The human samples assayed can be divided up into:
35 samples negative for total anti-*Treponema pallidum* immunoglobulins and anti-*treponema pallidum* IgM (double negatives).
3 samples positive for total anti-*Treponema pallidum* immunoglobulins and negative for anti-*Treponema pallidum* IgM (samples 1, 2, 3).
4 samples positive for anti-*Treponema pallidum* IgM and negative for total anti-*Treponema pallidum* immunoglobulins (samples 4, 5, 6, 7).

Methods

Assay Protocols:
The protocols used are identical to protocols A, B and C described above in example 2, with the exception of the volumes in step 1, which are 100 µl for the sample and 100 µl for the beads, and in step 2, which is 100 µl of solution of conjugate 1 (biotinylated *Treponema pallidum* antigens).

The other steps are identical, including the interpretation step.

Interpretation of the Results:
For the assaying of the total anti-*Treponema pallidum* Igs and the anti-*Treponema pallidum* IgMs, the cut-off value is the mean of the RFIs of the negative samples divided by 0.3.

The sample ratio calculated relative to the cut-off value is thus the following:

Sample ratio=mean*of the RFI signal of the sample cut-off value

The samples whose ratios are greater than or equal to 1 are declared positive, those for which the ratios are less than 1 are declared negative.

All the assays of human samples are carried out in triplicate and the RFI results used come from the mean of the three replicates.

Results Obtained:

TABLE 8

Comparison of the assaying of samples for total anti-*Treponema pallidum* Igs by unit sandwich format and by multiplex according to the invention

| | | Unit total Ig sandwich format | | Multiplex total Ig sandwich format | |
|---|---|---|---|---|---|
| | | RFI | Ratio | RFI | Ratio |
| Cut-off value mean negatives/0.3 | | 80 | 1.00 | 80 | 1.00 |
| Samples negative for anti-*Treponema pallidum* IgG and negative for anti-*Treponema pallidum* IgM Mean (n = 35) | | 24 | 0.30 | 24 | 0.30 |
| Samples positive for anti-*Treponema pallidum* IgG and negative for anti-*Treponema pallidum* IgM (n = 3) | 1 | 750 | 9.38 | 877 | 10.96 |
| | 2 | 2064 | 25.80 | 2417 | 30.21 |
| | 3 | 10471 | 130.89 | 13000 | 162.50 |

Very good discrimination is noted between the negative samples (n=35) and the positive samples (n=3) in the total anti-*Treponema pallidum* Ig sandwich assay, irrespective of whether it is carried out by unit format or by multiplex according to the invention.

These results thus show that the detection of total anti-*Treponema pallidum* Igs is not desensitized in the multiplex method according to the invention.

All the positive samples are indeed found to be positive by the method according to the invention, which thus makes it possible to also obtain good clinical sensitivity.

TABLE 9

Comparison of the assaying of samples for anti-*Treponema pallidum* IgM by unit immunocapture format and by multiplex immunocapture format according to the invention

|  |  | Unit IgM immunocapture format | | Multiplex IgM immunocapture format | |
|---|---|---|---|---|---|
|  |  | RFI | Ratio | RFI | Ratio |
| Cut-off value mean negatives/0.3 |  | 150 | 1.00 | 152 | 1.00 |
| Samples negative for anti-*Treponema pallidum* IgG and anti-*Treponema pallidum* IgM Mean (n = 35) |  | 45 | 0.30 | 46 | 0.30 |
| Samples positive for anti-*Treponema pallidum* IgG and negative for anti-*Treponema pallidum* IgM (n = 3) | 1 | 38 | 0.25 | 38 | 0.25 |
|  | 2 | 51 | 0.34 | 58 | 0.38 |
|  | 3 | 38 | 0.25 | 41 | 0.27 |
| Samples positive for anti-*Treponema pallidum* IgM and negative for (total) anti-*Treponema pallidum* IgG (n = 4) | 4 | 286 | 1.91 | 241 | 1.59 |
|  | 5 | 185 | 1.23 | 192 | 1.26 |
|  | 6 | 996 | 6.64 | 884 | 5.82 |
|  | 7 | 293 | 1.95 | 324 | 2.13 |

Very good discrimination is noted between the samples negative for anti-*Treponema pallidum* IgM (n=35+3) and the samples positive for anti-*Treponema pallidum* IgM (n=3) in the anti-*Treponema pallidum* IgM assay by immunocapture, irrespective of whether it is carried out by unit format or by multiplex according to the invention.

These results thus show that the detection of IgMs by immunocapture is not desensitized by the combination with the sandwich assay in the multiplex method according to the invention.

All the positive samples are indeed found to be positive by the method according to the invention, which thus makes it possible to obtain good clinical sensitivity.

In conclusion, the results obtained in examples 2, 3 and 4 using the multiplex method according to the invention, which combines IgM detection by immunocapture and total Ig detection by sandwich, clearly show that the method according to the invention allows sensitive detection and differentiation of total Ig class antibodies or of IgGs and of IgMs, directed against the same microorganism. Those skilled in the art will readily conclude therefrom that the method for the multiplex detection of IgGs and IgMs according to the invention is in fact a method of general scope, that can be adapted to many microorganisms for which it is important, from a diagnostic point of view, to detect total Igs and IgMs.

Furthermore, the method of the invention can be readily automated through the use of an automated device, such as, for example, BioPlex 2200 from Bio-Rad, which enables the assay protocols to be carried out simultaneously and rapidly, in a single receptacle, and the signals to be read in a single step.

We claim:

1. An in vitro method for the detection of antibodies directed against a microorganism present in a biological sample comprising:
   a) forming a mixture, in a single assay receptacle, comprising a biological sample and at least two groups of particles, said at least two groups of particles comprising a first particle group carrying an anti-IgM capture antibody that specifically binds to IgM and a second particle group carrying a capture antigen derived from a microorganism,
   b) incubating the mixture under conditions which allow the formation of immunocomplexes on each group of particles,
   c) eliminating from the mixture of step b) the immunoglobulins of the biological sample which have not bound to particles,
   d) incubating the particles of step c) with at least one labelled conjugate to form an immunocomplex-conjugate mixture on said particles, said at least one labelled conjugate comprising a detection antigen derived from said microorganism conjugated to a label,
   e) eliminating from the mixture of step d) the detection antigen not bound to the immunocomplex conjugates on the particles, and
   f) simultaneously detecting immunocomplexes formed on each particle group with a detector capable of differentiating particle groups, and determining the presence or the amount of immunoglobulin G (IgG) or total immunoglobulin and immunoglobulin M (IgM) directed against said microorganism in said biological sample.

2. The method according to claim 1, wherein the presence or the amount of immunoglobulin G (IgG) or total immunoglobulin and/or immunoglobulin M (IgM) is an indication of an infection with said microorganism.

3. The method according to claim 1, wherein the antigen derived from the microorganism is selected from the group consisting of a lysate of said microorganism, a natural antigen that has been semi-purified or purified from a microorganism, a recombinant protein, a fragment thereof and a synthetic peptide.

4. The method according to claim 1, wherein said groups of particles differ from one another by virtue of fluorochromes, detectable by a suitable detector.

5. The method according to claim 1, wherein the detector is a flow cytometer.

6. The method according to claim 1, wherein the detection antigen carries a biotin which is detected by adding labelled avidin or labelled streptavidin.

7. The method according to claim 1, wherein the biological sample is plasma or serum.

8. The method according to claim 1, wherein the biological sample is of human origin.

9. The method according to claim 1, wherein said microorganism is selected from the group consisting of viruses, bacteria and single-cell parasites.

10. The method according to claim 9, wherein said microorganism is a human hepatitis virus.

11. The method according to claim 10, wherein said microorganism is a human hepatitis A virus (HAV) or a human hepatitis B virus (HBV).

12. The method according to claim 11, wherein said microorganism is the human hepatitis A virus (HAV) and a lower detection limit for total anti-HAV immunoglobulins of approximately 20 mIU/ml is obtained.

13. The method according to claim 1, wherein at least one group of particles comprises superparamagnetic particles.

14. The method according to claim 1, wherein said immunoglobulins of the biological sample which have not bound to the particles or said detection antigen which has not bound to the immunocomplex conjugates on the particles is eliminated by washing said particles.

15. A method for the in vitro detection of an infection with a microorganism comprising:

a) forming a mixture, in a single assay receptacle, comprising a biological sample and at least two groups of particles, said at least two groups of particles comprising a first particle group carrying an anti-IgM capture antibody that specifically binds to IgM and a second particle group carrying a capture antigen derived from a microorganism, b) incubating the mixture under conditions which allow the formation of immunocomplexes on each group of particles, c) eliminating from the mixture of step b) the immunoglobulins of the biological sample which have not bound to particles, d) incubating the particles of step c) with at least one labelled conjugate to form an immunocomplex-conjugate mixture on said particles, said at least one labelled conjugate comprising a detection antigen derived from said microorganism conjugated to a label, e) eliminating from the mixture of step d) the detection antigen not bound to the immunocomplex conjugates on the particles, and f) simultaneously detecting immunocomplexes formed on each particle group with a detector capable of differentiating particle groups, the presence or the amount of immunoglobulin (IgG) or total immunoglobulin and/or immunoglobulin M (IgM) directed against said microorganism indicating an infection by said microorganism.

16. A method for the in vitro diagnostic detection of an infection with a microorganism comprising:

a) forming a mixture, in a single assay receptacle, comprising a biological sample and at least two groups of particles, said at least two groups of particles comprising a first particle group carrying an anti-IgM capture antibody that specifically binds to IgM and a second particle group carrying a capture antigen derived from a microorganism, b) incubating the mixture under conditions which allow the formation of immunocomplexes on each group of particles, c) eliminating from the mixture of step b) the immunoglobulins of the biological sample which have not bound to particles, d) incubating the particles of step c) with at least one labelled conjugate to form an immunocomplex-conjugate mixture on said particles, said at least one labelled conjugate comprising a detection antigen derived from said microorganism conjugated to a label, e) eliminating from the mixture of step d) the detection antigen not bound to the immunocomplex conjugates on the particles, and f) simultaneously detecting immunocomplexes formed on each particle group with a detector capable of differentiating particle groups, the presence or the amount of immunoglobulin G (IgG) or total immunoglobulin and/or immunoglobulin M (IgM) directed against said microorganism indicating an infection by said microorganism.

* * * * *

UNITED STATES PATENT AND TRADEMARK OFFICE
CERTIFICATE OF CORRECTION

PATENT NO. : 9,523,685 B2  
APPLICATION NO. : 13/892521  
DATED : December 20, 2016  
INVENTOR(S) : Christine Charpentier et al.

Page 1 of 1

It is certified that error appears in the above-identified patent and that said Letters Patent is hereby corrected as shown below:

In the Specification

Column 13,  
Line 29, "Term.," should read --Tenn.,--.

Column 14,  
Line 49, "All" should read --* All--.

Column 15,  
Line 54, "Term.," should read --Tenn.,--.

Column 17,  
Line 22, "All" should read --* All--.  
Line 45, "All" should read --* All--.

Column 21,  
Line 38, "All" should read --* All--.

Column 24,  
Line 20, "All" should read --* All--.

Signed and Sealed this  
Eighteenth Day of July, 2017

Joseph Matal  
*Performing the Functions and Duties of the*  
*Under Secretary of Commerce for Intellectual Property and*  
*Director of the United States Patent and Trademark Office*